US007407670B2

(12) United States Patent
Six et al.

(10) Patent No.: US 7,407,670 B2
(45) Date of Patent: Aug. 5, 2008

(54) SOLID DISPERSIONS COMPRISING TWO DIFFERENT POLYMER MATRIXES

(75) Inventors: Karel Six, Boortmeerbeek (BE); Geert Verreck, Malle (BE); Jozef Peeters, Beerse (BE); Marcus Eli Brewster, Beerse (BE); Guy Van Den Mooter, Pellenberg (BE)

(73) Assignee: Janssen Pharmaceutica, N.V., Beerse (BE)

( * ) Notice: Subject to any disclaimer, the term of this patent is extended or adjusted under 35 U.S.C. 154(b) by 0 days.

(21) Appl. No.: 10/518,987

(22) PCT Filed: Jul. 1, 2003

(86) PCT No.: PCT/EP03/06999

§ 371 (c)(1),
(2), (4) Date: Dec. 21, 2004

(87) PCT Pub. No.: WO2004/004683

PCT Pub. Date: Jan. 15, 2004

(65) Prior Publication Data

US 2006/0062809 A1    Mar. 23, 2006

(30) Foreign Application Priority Data

Jul. 4, 2002    (WO) ................. PCT/EP02/07422

(51) Int. Cl.
*A61K 9/14*    (2006.01)
(52) U.S. Cl. .................................... 424/486
(58) Field of Classification Search ........................ None
See application file for complete search history.

(56) References Cited

FOREIGN PATENT DOCUMENTS

| WO | WO 97/44014 A1 | 11/1997 |
| WO | WO 99/33467 A1 | 7/1999 |
| WO | WO 9933467 A1 * | 7/1999 |
| WO | WO 02/11694 A2 | 2/2002 |

OTHER PUBLICATIONS

T. Matsumoto et al., Pharm. Res., 16 (1999) 1722-2728.
G. Van den Mooter et al., Eur. J. Pharm. Sci. 12 (2001) 261-269.
G.L. Amidon et al., Pharm. Res., 12 (1995) 413-420.
K. Six et al., Int. J. Pharm., 213 (2001) 163-173.
S. Gordon et al., Appl. Chem. 2 (1952) 493-500.
F.N. Kelley et al., J. Pol. Sci. 50 (1961) 549-556.
R. Simha et al., J. Chem. Phys. 37 (1962) 1003-1007.
F. Damian et al., J. Pharmacy and Pharmacology (2001) 53: 1109-1116.
G. Van den Mooter et al., Thermal Analysis and Calorimetry (1999), 57, 493-507.
K. Six et al., Thermochim. acta, 376 (2001), 175-181.
B.C. Hancock et al., Pharm. Res., vol. 17, No. 4 (2000) 397-404.
M. Tros de Llarduya et al., Drug Dev. Ind. Pharm (1998) 24:295-300.
PCT Search Report for PCT/EP03/06999 dated Nov. 12, 2003.

* cited by examiner

*Primary Examiner*—Sandra Saucier
*Assistant Examiner*—Satyendra K Singh
(74) *Attorney, Agent, or Firm*—Woodcock Washburn LLP

(57) ABSTRACT

Present invention provides solid dispersions comprising a poorly soluble bioactive compound dispersed in a polymer matrix characterized in that the polymer matrix comprises more than one polymer. Said solid dispersions effectively stabilize the dispersed compound while stimulating the solubilisation of the compound in an aqueous environment.

16 Claims, 13 Drawing Sheets

SOLID DISPERSIONS COMPRISING TWO DIFFERENT POLYMER MATRIXES

CROSS REFERENCE TO RELATED APPLICATIONS

Figure 1:
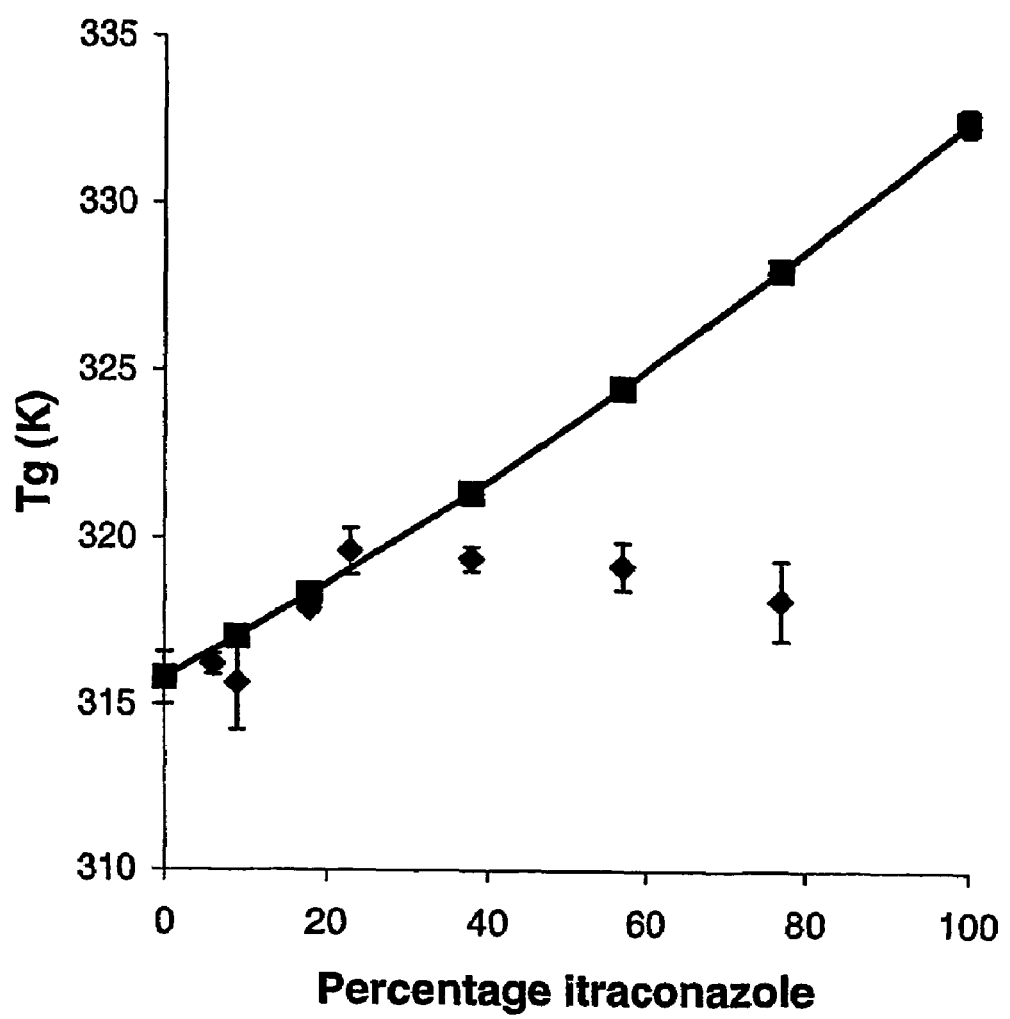

This application is the national stage of Application No. PCT/EP03/06999, filed Jul. 1, 2003, which application claims priority from PCT/EP02/07422 filed Jul. 4, 2002.

FIELD OF THE INVENTION

Present invention provides solid dispersions comprising a poorly soluble bioactive compound dispersed in a polymer matrix characterized in that the polymer matrix comprises more than one polymer. Said solid dispersions effectively stabilize the dispersed compound while stimulating the solubilisation of the compound in an aqueous environment.

BACKGROUND OF THE INVENTION

It is generally recognized that the following four factors compromise the oral bioavailability of drugs from solid dosage forms: I) low solubility and/or dissolution rate in the gastrointestinal (GI) tract, ii) low membrane permeability, iii) interaction with components of the GI tract leading to complex formation, and iv) metabolism in the liver, the GI lumen or in the GI mucosa (either membrane or cytosol related). Drugs having a dissolution—limited oral absorption might benefit from a reduction in particle size, as well as from an increase in saturation solubility, as pointed out in the following equation which is a modification of the well known Noyes-Whitney relation:

$$\frac{dM}{dt} = \frac{AD(C_s - C_t)}{h}$$

where dM/dt is the dissolution rate, A the specific surface area of the drug particle, D the diffusion coëfficient, h the diffusion layer thickness, $C_s$ the saturation solubility, and $C_t$ the drug concentration at time t. Both principles form the rationale for the use of solid dispersions, a possible pharmaceutical strategy that can result in increased solubility and dissolution rate. The term refers to a dispersion of one or more active ingredients in an inert and hydrophilic carrier or matrix in the solid state, prepared by melting (fusion) or solvent method. The presence of the carrier not only prevents aggregation/agglomeration of individual drug particles exhibiting a high solid-liquid surface tension, it also creates a micro-environment in which the drug solubility is high. Solid dispersions are physico-chemically classified as eutectics, solid solutions, glass solutions and suspensions, amorphous precipitates in a glassy or crystalline carrier, complex formations, and/or a combination of the different systems. Although the use of solid dispersions has been reported frequently in the pharmaceutical literature, very few marketed products rely on the solid dispersion strategy. The main reason for this discrepancy is the physical instability (aging effects) of these structures which ate often metastable. Phase separation, crystal growth or conversion from the amorphous (metastable) to the crystalline state during storage, inevitably results in decreased solubility and dissolution rate.

The presence of the carrier (often a polymer) is often adequate to prevent recrystallization. Recently, it was stated by Motsumoto and Zografi [1] that stabilization of amorphous indomethacin in PVP and PVPVA64 dispersions was mainly the consequence of drug-polymer interactions, while Van den Mooter et al. [2] clearly showed that the antiplasticizing effect of those polymers in dispersions with ketoconazole was the only stabilizing factor. A proper choice of polymer will increase the glass transition temperature (Tg) of the binary system in a way that the molecular mobility becomes extremely low at room temperature hence leading to acceptable physical stability. This increase in Tg is only occurring when the drug is completely dissolved (dispersed at molecular level) in the polymer with the absence of free glassy or crystalline drug.

Besides the homogeneous dispersion (at molecular level) of the drug in the polymer matrix, we hypothesize that the intrinsic dissolution properties of the polymer are also important. The polymer should dissolve slowly enough so that the drug is able to go into solution together with the polymer. Indeed in this way the polymer can create a microenvironment where the drug solubility is favored. This is of course only valid if a polymer is selected that will increase the solubility of the drug in the aqueous environment. The microenvironment is not adequate if the polymer dissolves too fast. On the other hand too slow a dissolution rate of the polymer will result in too slow a release of the drug. Taking the above mentioned considerations into account we selected several carriers (polymers) to prepare solid dispersions showing physical stability and improved dissolution properties. In order to challenge the selected polymers, itraconazole was chosen as a model drug. It is known that this drug (classified as a class II drug in the BCS) [3] has an extremely low aqueous solubility and dissolution rate The aim of the present invention describes the dissolution properties (pharmaceutical performance) and physical properties of solid dispersions of itraconazole and a fast (PVPVA64), a slow (eudragit E100) dissolving polymer, and combinations thereof prepared by hot-stage extrusion.

SUMMARY OF THE INVENTION

A first object of the present invention is a solid dispersion comprising a poorly soluble bioactive compound dispersed in a polymer matrix, comprising more than one polymer, characterized in that a first polymer allows a homogenous or molecular dispersion of the bioactive compound in the polymer matrix, while a second polymer allows the enhancement of the dissolution of the bioactive compound in an aqueous environment. In a preferred embodiment at least one of the polymers has a stabilizing effect on the bioactive compound in solution.

Preferably the polymers promoting the homogenous or molecular dispersion of the bioactive compound in the polymer matrix are selected from the group comprising PVPVA64.

Preferably the polymers having a dissolution rate, which creates a micro-environment enhancing the dissolution of the bioactive compound, are selected from the group comprising hydrox-propyl-methyl cellulose, Eudragit E100.

In a more preferred embodiment the polymer matrix comprises Eudragit E100 and PVPVA64. In a most preferred embodiment the polymer matrix comprises Eudragit E100 and PVPVA64 in a Eudragit E100/PVPVA64 ratio varying between 70/30 and 80/20.

ILLUSTRATIVE EMBODIMENT OF THE INVENTION

Definitions

"poorly soluble compounds" refers to compounds having a solubility lower than 1 g/l in an aqueous environment.

"Microenvironment" refers to the area near the surface of a dissolving polymer as well as to the physico-chemical conditions characterizing said area.

LEGENDS TO THE FIGURES

FIG. 1: Experimental (♦) and theoretical (■) values of Tg calculated by the Gordon-Taylor/Kelley-Bueche equation of itraconazole-eudragit E100 dispersions prepared at 453K, followed by milling.

Figure 2:
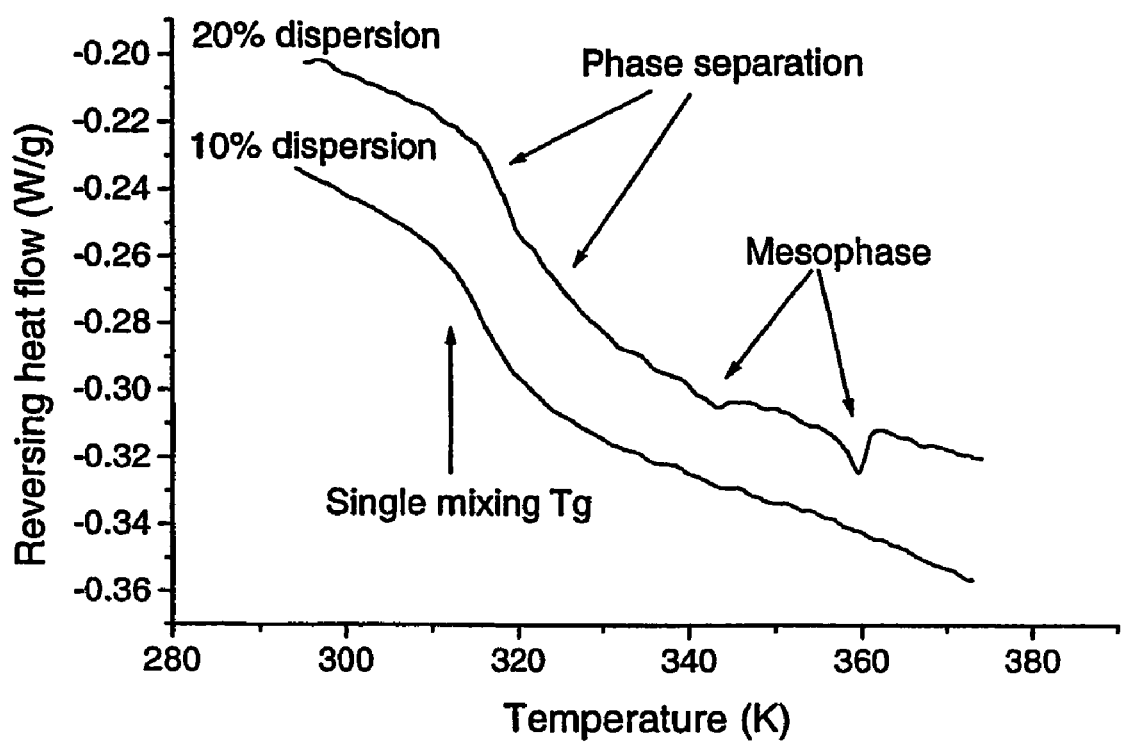

FIG. 2: Reversing heat flow of a 10 and 20% w/w solid dispersion (itraconazole/eudragit E100) prepared at 453K, followed by milling FIG. 3: Powder X-ray diffraction pattern of dispersions (itraconazole/eudragit E100) extruded at 413K FIG. 4: Total heat flow of 25% dispersion (itraconazole/eudragit E100) prepared at 413K and milled showing cold crystallization upon heating FIG. 5: Reversing heat flow of solid dispersions in PVPVA64 with different drug loading versus temperature.

Figure 6:
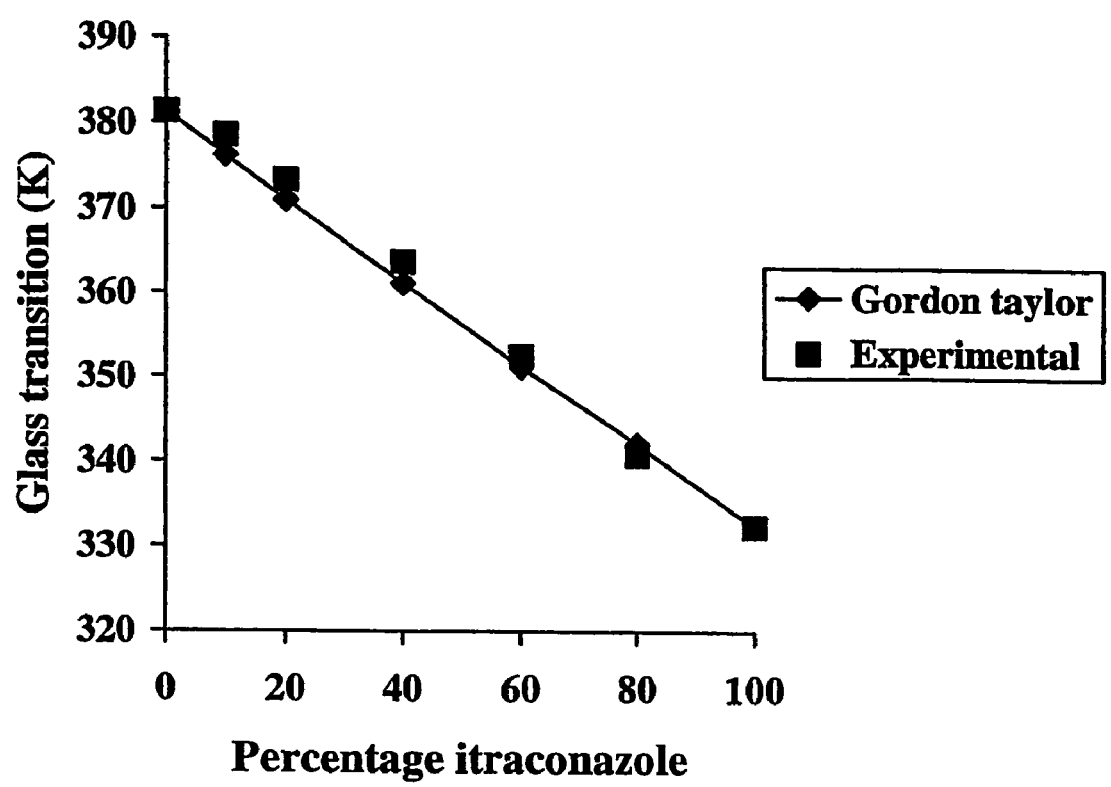

FIG. 6: Comparison of experimental and theoretical glass transition temperatures calculated with the Gordon-Taylor equation of itraconazole/PVPVA64 dispersions.

Figure 7:
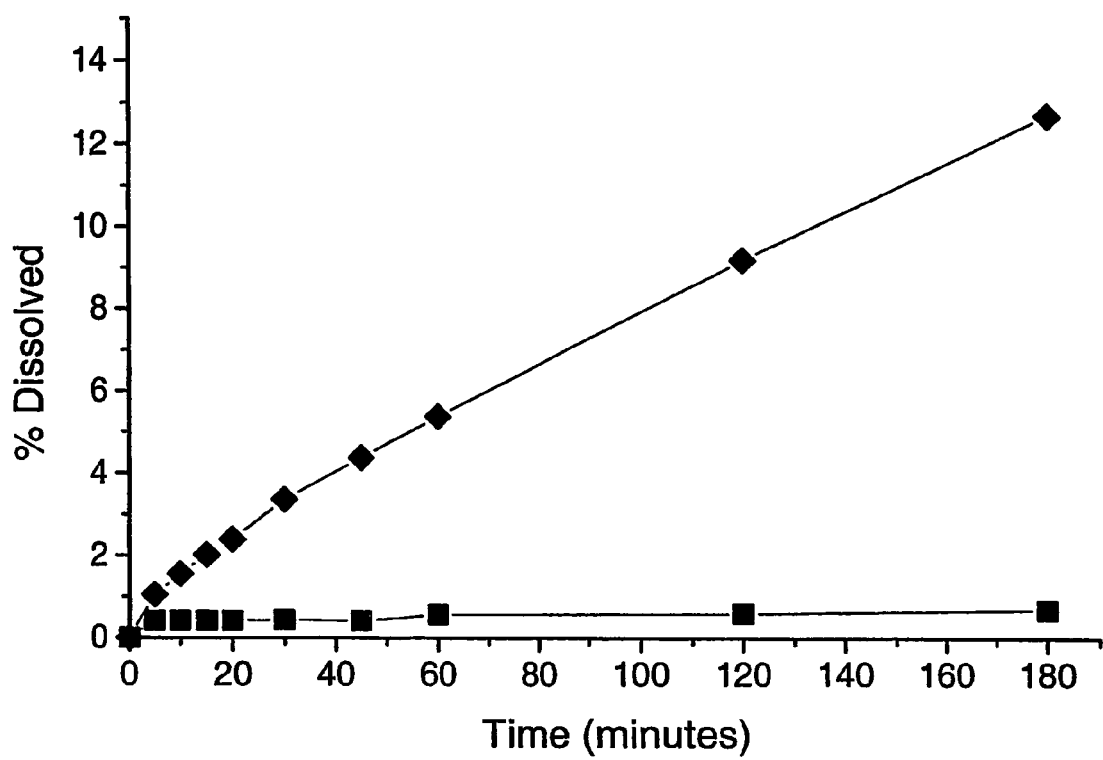

FIG. 7: Comparison of the dissolution of crystalline and glassy itraconazole in simulated gastric fluid (♦=glassy itraconazole, ■=crystalline itraconazole).

Figure 8:
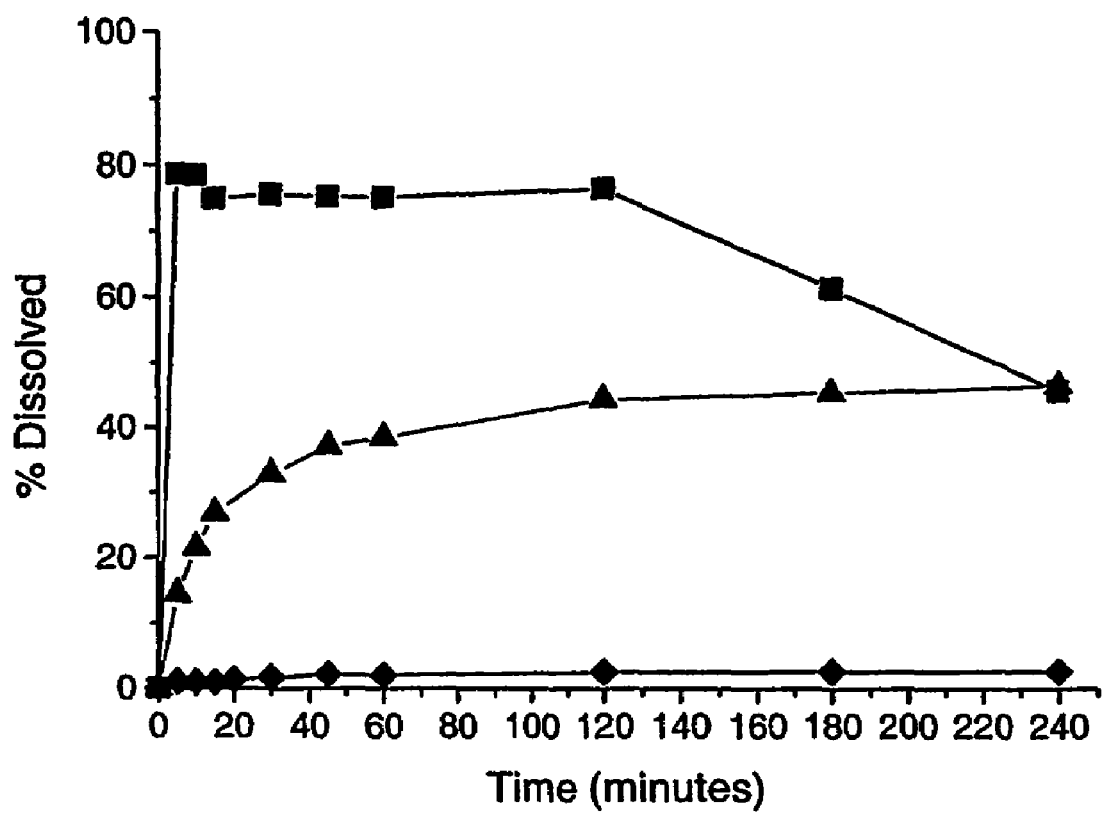

FIG. 8: Dissolution profiles of a 40% itraconazole w/w solid dispersion with eudragit E100 (■), PVPVA64 (▲) and a physical mixture (itraconazole/eudragit E100) (♦) in simulated gastric fluid.

Figure 9:
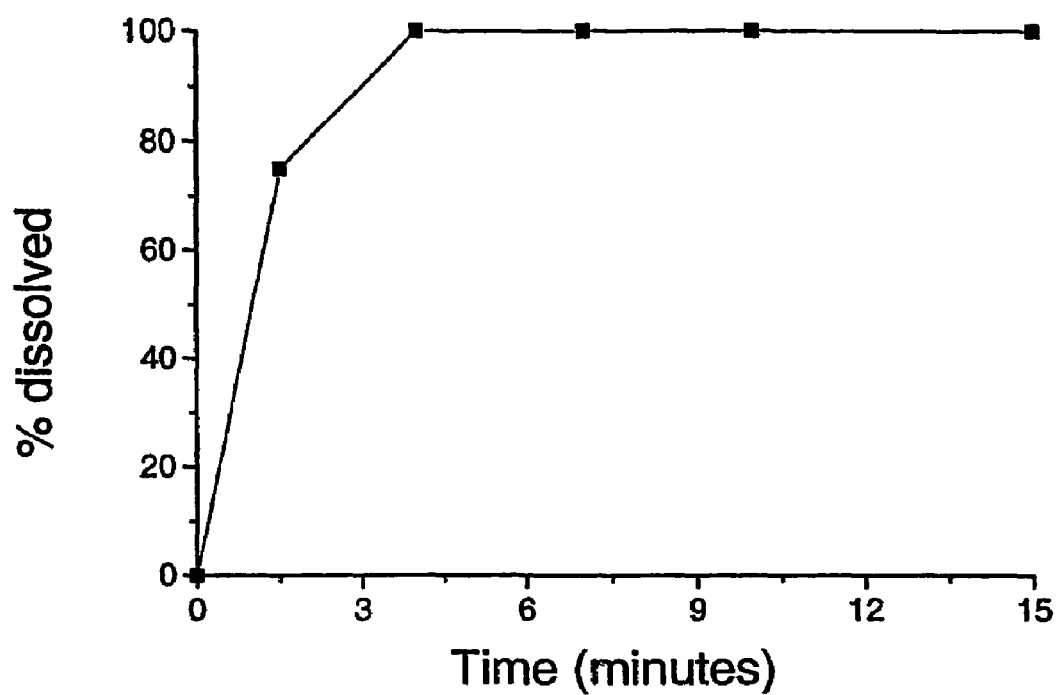

FIG. 9: Dissolution profile of pure PVPVA64 in simulated gastric fluid.

Figure 10:
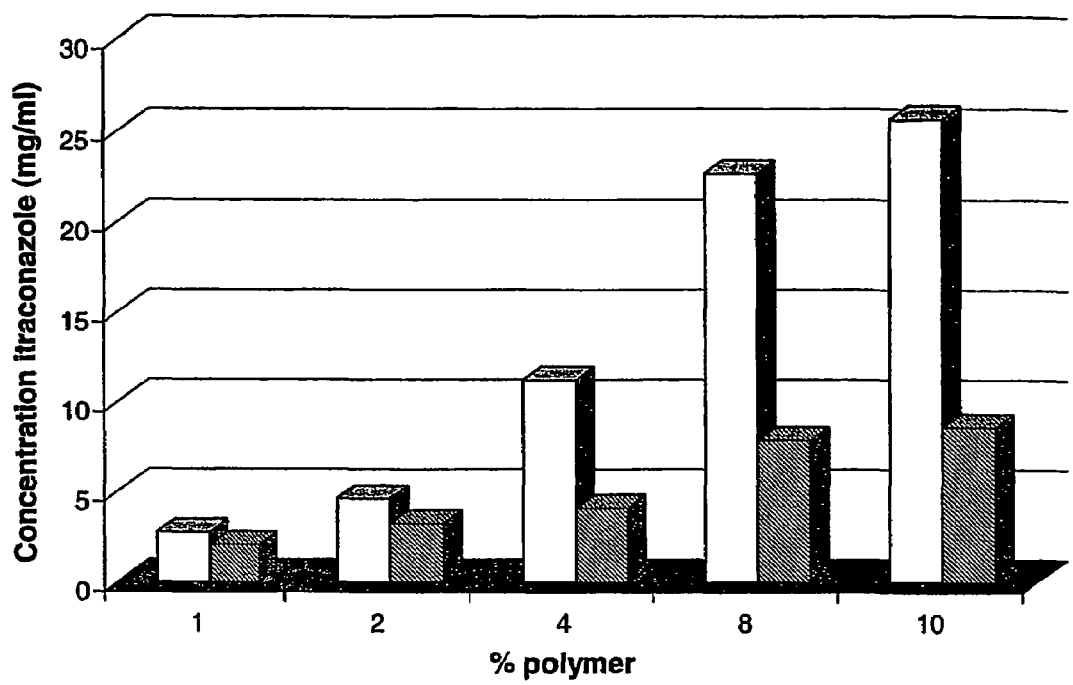

FIG. 10: Solubility of itraconazole in different concentration of polymer solutions at 298K in eudragit E100 (open bars) and PVPVA64 (closed bars).

Figure 11:
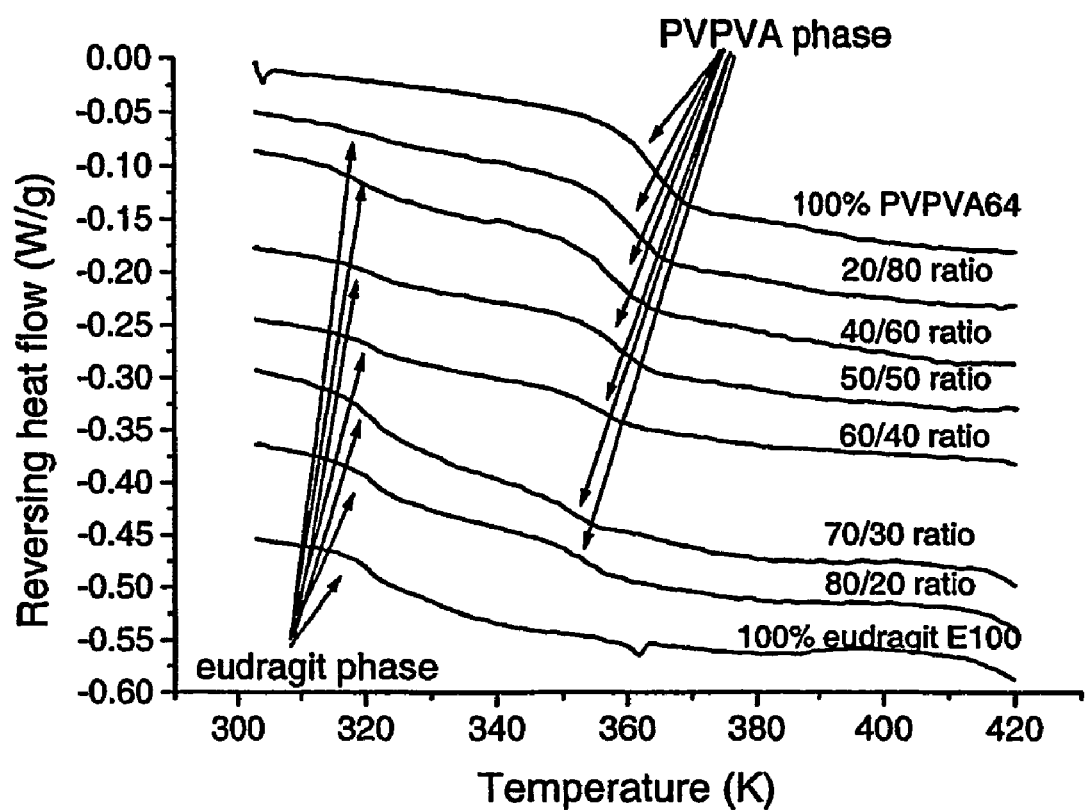

FIG. 11: Reversing heat flow of solid dispersions with 40% itraconazole and different eudragit E100/PVPVA64 ratio's.

Figure 12:
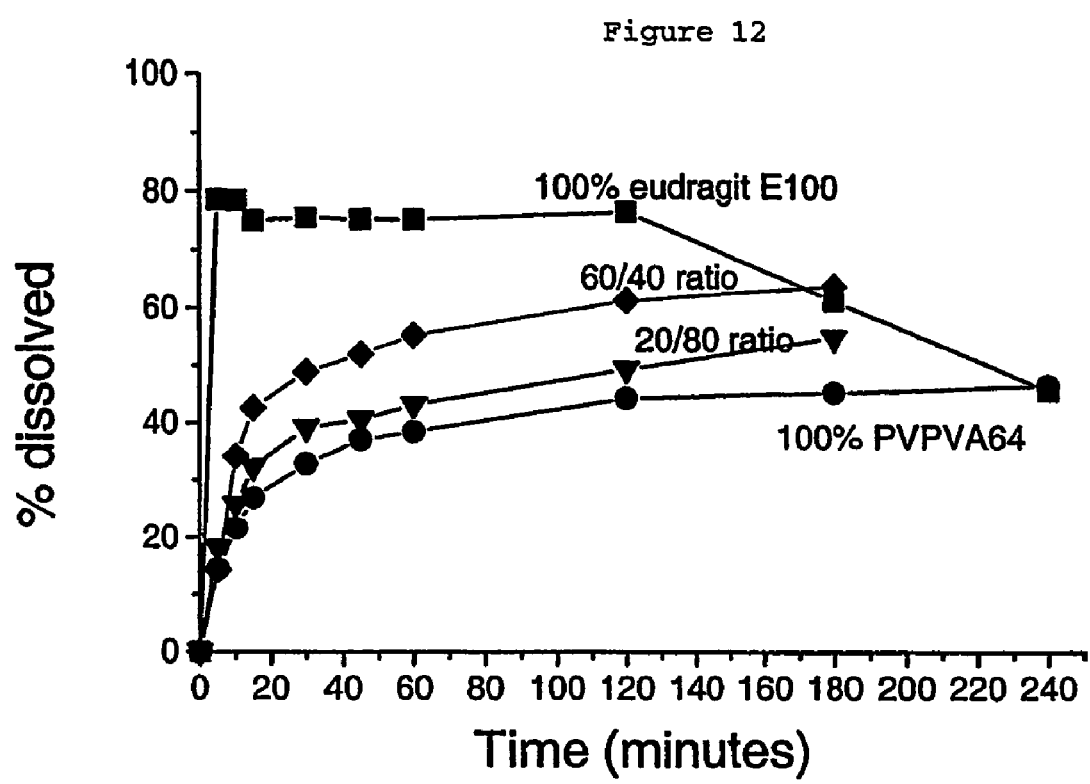

FIG. 12: Dissolution profile of 40% w/w itraconazole in 20/80 and 60/40 eudragit E100/PVPVA64 ratio and in 100% eudragit E100 and PVPVA64.

Figure 13:
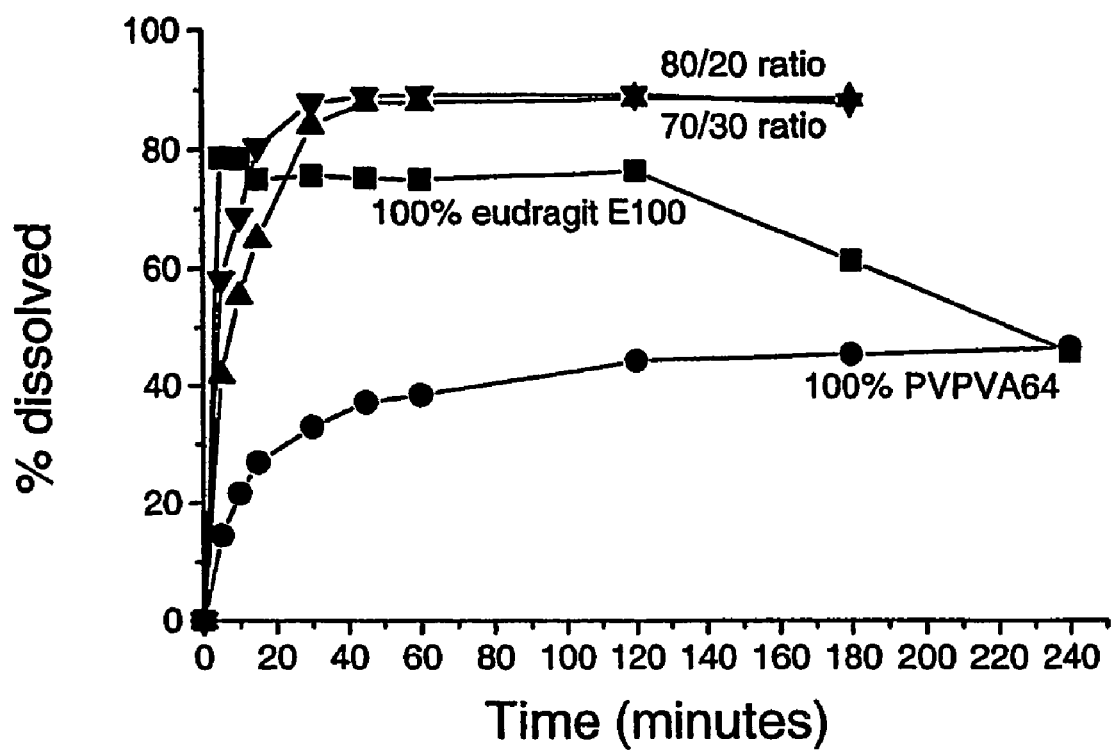

FIG. 13: Dissolution profile of 40% w/w itraconazole in 80/20 and 70/30 eudragit E100/PVPVA64 ratio and in 100% eudragit E100 and PVPVA64

MATERIALS AND METHODS

Materials

Itraconazole (<355 μm) (purity more than 99%) was kindly donated by Janssen Pharmaceutica (Beerse, Belgium), eudragit E100 and PVPVA64 were obtained from Röhm (Germany) and BASF (Ludwigshafen, Germany) respectively.

Hot-stage Extrusion

Hot-stage extrusion was performed with a co-rotating twin screw extruder MP19 PH 25:1 (APV, UK). The screw-configuration consisted of two mixing zones and three transport zones over the whole barrel length; the screw rate was 300 rpm. Experiments were performed at different temperature settings depending on the polymer and taking in to account that the last two zones were above the melting point of itraconazole (441K). The extrudates were collected after cooling at ambient temperature on a conveyer belt. Samples were milled for 1 minute with a laboratory-cutting mill (Kika, Germany) and sieved to exclude particles >355 μm.

All samples were stored in a desiccator at room temperature and analyzed within 3 weeks.

Modulated Temperature DSC (MTDSC)

MTDSC measurements were carried out using a 2920 Modulated DSC (TA Instruments, Leatherhead, UK), equipped with a refrigerated cooling system (RCS). Data were treated mathematically using the Thermal Solutions software (TA Instruments, Leatherhead, UK). Dry helium at a flow rate of 40 ml/min was used as the purge gas through the DSC cell and 150 ml/min of nitrogen was used through the RCS unit. TA Instruments (Leatherhead, UK) aluminum open pans were used for all calorimetric studies; the mass of each empty sample pan was matched to the mass of the empty reference pan within ±0.1 mg.

The amplitude used was 0.212K, the period 40 s and the underlying heat rate 2K/min [4]. Octadecane, benzoic acid, cyclohexane and indium standards were used to calibrate the DSC temperature scale; enthalpic response was calibrated with indium. The heat capacity signal was calibrated by comparing the response of dry, powdered aluminum oxide to the equivalent literature value in the glass transition region of itraconazole. Validation of temperature, enthalpy and heat capacity measurement using the same standard materials showed that deviation of the experimental from the reference value was less than 0.5K for temperature measurement, less than 0.1% for enthalpy measurement and less than 0.7% for measurement of the heat capacity at 329.8K.

Powder X-ray Diffraction

Powder X-ray diffraction was performed with a Philips PW Diffractometer (beam 173 mm). Monochromatic Cu $K_{\alpha 1}$ radiation (λ 1.5406 Å) was obtained with a Ni filtration and a system of diverging, receiving and scattering slides of 1°, 0.2 mm and 1°, respectively. The diffraction pattern was measured with a voltage of 45 kV and a current of 20 mA in the region of 4°<2 θ<65° in a step scan mode of 0.2° every second.

Preparation of Glassy Itraconazole

Glassy itraconazole was prepared by melting crystalline itraconazole followed by rapid cooling to room temperature after which it was milled and sieved (<355 μm). Glassy itraconazole was stored in a desiccator at room temperature till further analysis (within 1 week).

Preparation of Physical Mixtures

Physical mixtures were prepared by mixing itraconazole and the polymer in a mortar for 5 minutes followed by sieving (<355 μm).

Dissolution Testing

Dissolution experiments were performed using the USP 24 method 2 (paddle method) in a Hanson SR8plus (Chatsworth, USA). In order to compare the dissolution properties of the extrudates, physical mixtures and pure itraconazole, 500 ml of simulated gastric fluid sine pepsin (USP 24) is used as dissolution medium at a temperature of 310.0K and a paddle speed of 100 rpm. Powdered extrudates and physical mixtures (always containing 200 mg itraconazole) or pure glassy itraconazole was added to the dissolution medium. 5 ml samples were taken and immediately replaced with fresh dissolution medium at 5, 10, 15, 30, 45, 60, 120, 180, 240 minutes, filtered with a Teflon filter of 0.5 μm (Fluoropore membrane filters Millipore, Ireland) whereby the first 2 ml were discarded, diluted with mobile phase (see below) 1 to 10 and analyzed using HPLC.

HPLC Analysis

HPLC-analysis was performed using a Merck Hitachi pump L7100, a UV detector L7400, a autosampler L7200 and a interface D7000 Merck, Darmstadt, Germany) and the peak areas were calculated using HSM software (Merck, Darmstadt, Germany). The column used was Lichrospher 100 RP-18 12.5×4 (5 µm) (Merck, Darmstadt, Germany); Acetonitrile/tetrabutyl ammonium hydrogen sulphate 0.1N (55:45; v/v) was used as mobile phase at a flow rate of 1.0 ml/min; UV detection was used at a wavelength of 260 nm. These conditions resulted in a typical elution time for itraconazole of 4.8 minutes.

Results and Discussion

In order to stabilize the high-energy form of the glassy class II drug, we prepared several solid (molecular) dispersions by hot-stage extrusion using a co-rotating twin screw extruder. The extrudates were milled for a very short period of time to avoid heating of the samples, which could cause recrystallization of the glassy drug and flow of the polymer, which in time could lead to major changes in the properties of the solid dispersions. The thermodynamic properties of the milled and unmilled samples were examined by modulated temperature DSC (MTDSC).

FIG. 1 shows the experimental and theoretical values of Tg for extrudates with itraconazole and eudragit E100, an example of a slowly dissolving polymer, prepared at 453.0K, followed by milling for 1 minute using a laboratory scale mill. The theoretical values were calculated using the Gordon-Taylor/Kelly-Bueche equation [5, 6]:

$$Tg_x = \frac{Tg_1 w_1 + Tg_2 K w_2}{w_1 + K w_2}$$

in which $Tg_1$ and $Tg_2$ are the glass transition temperature of eudragit E100 (315.9K) and itraconazole (332.4K), respectively, $w_1$ and $w_2$ are the weight fractions of eudragit E100 and itraconazole in the dispersions, respectively, and K is a constant which was calculated using the Simha-Boyer rule [7]:

$$K \cong \frac{\rho_1 Tg_1}{\rho_2 Tg_2}$$

Where ρ is the density of the amorphous solids

The densities are 1.09 and 1.27 for Eudragit E100 and glassy itraconazole, respectively and K is calculated to be 0.82.

Although the Gordon-Taylor relationship was originally derived for compatible polymer blends, it has been used successfully for small organic molecules as well [1, 2, 8, 9]. For dispersions prepared with eudragit E100 the experimental values coincide with the theoretical ones until approximately 20% w/w of drug, but from that point on the Tg's remains more or less constant and deviate significantly from the theoretical values (FIG. 1). Given the chemical structures of itraconazole and Eudragit E100, it is unlikely that this deviation is caused by drug-polymer interactions. Moreover, dispersions containing 15% w/w or higher of drug were opaque, in contrast to those with lower drug concentration which were completely transparent. This observation prompted us to investigate the possibility of phase separation in the dispersions. Powder X-ray diffraction experiments at room temperature indicated the absence of crystallinity in the dispersions up to 80% w/w of drug (data not shown), this suggest that the separated phases are amorphous. FIG. 2 shows the reversing heat flow signal of a dispersion containing 10 and 20% w/w of drug. At 10% w/w, one single Tg was observed indicating phase miscibility, but from 20% w/w of drug on, the dispersions clearly show two Tg's, one of glassy itraconazole at 332.4K and one originating from the drug-polymer mixture.

In addition the endothermic signal at 363.0K is caused by the pure glassy itraconazole phase and corresponds to the transition from the chiral nematic mesophase to the isotropic liquid [10] and confirms phase separation. Further heating of the dispersions containing 20% w/w or more of drug led to cold crystallisation into pure itraconazole (melting point 441.2K). These observation indicate that eudragit E100 only protects that part of the drug from recrystallization which is mixed with the carrier (molecular dispersed); Clusters of free drug are not protected and recrystallize. This observation confirms the inadequate stabilization of a polymer when both phases are not completely mixed. Basic thermodynamics suggests that the occurrence of phase separation will have a major influence on the physical stability of the drug in such dispersions.

Figure 3:
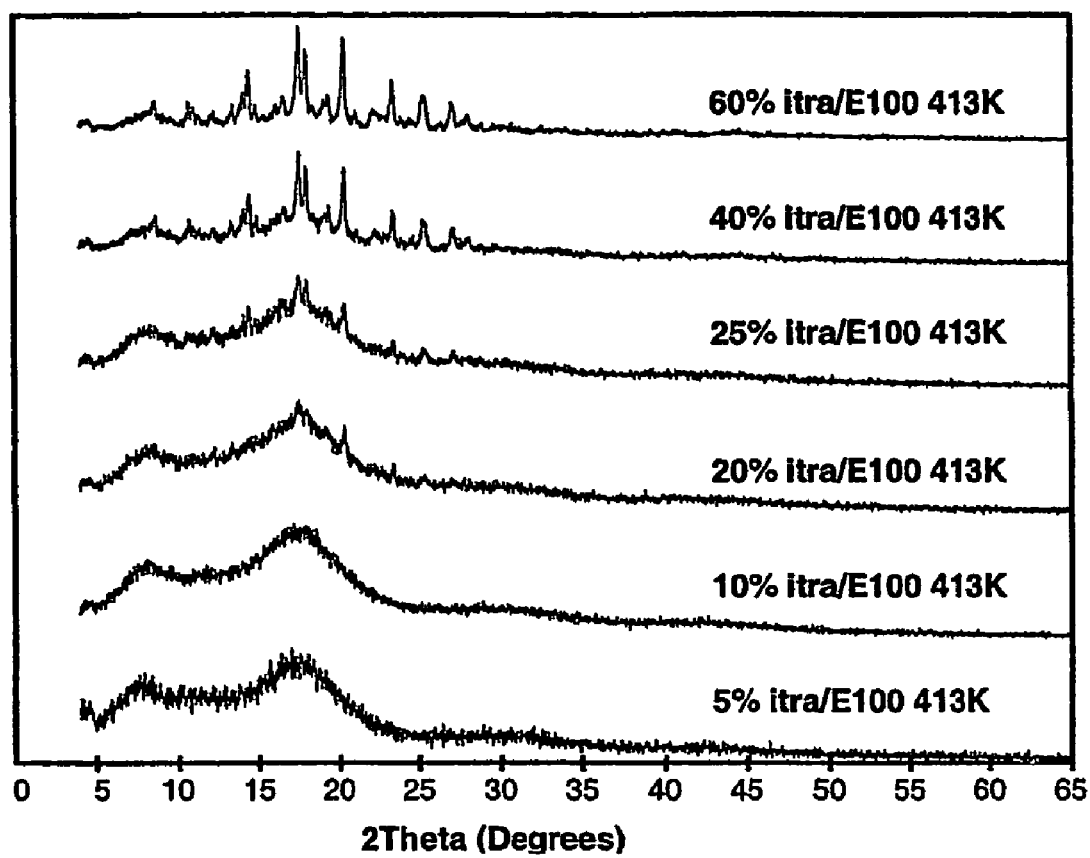
Figure 4:
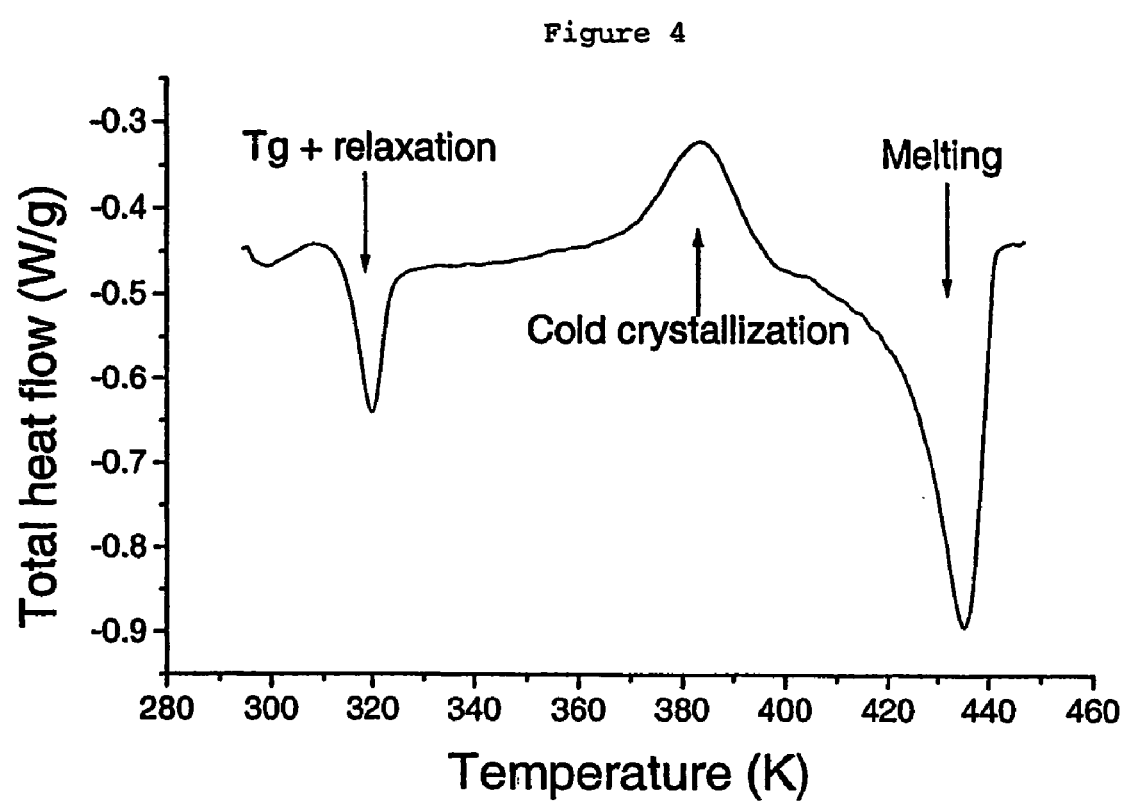

In order to further explore the phase separation, extrudates were also prepared at 413.0K which is 28.0K below the melting point of itraconazole. The same trends were observed as with dispersions prepared at 453.0K, i.e. transparent dispersions up to approximately 15% w/w of drug. Up to 15% the physical properties of both preparation modes are completely identical in MTDSC and X-ray diffraction experiments (data not shown), but above 15%, opacity was observed. However, in contrast to the extrudates prepared at 453.0K, powder X-ray diffraction experiments showed diffraction lines typical for crystalline itraconazole at ≧20% w/w of drug (FIG. 3). These dispersions also recrystallised upon heating (FIG. 4). Calculation of the initial crystallinity of the drug in these dispersions was based on the enthalpy of fusion and recrystalisation as described in detail by Van den Mooter et al. [2]. Subtraction of the initial crystallinity from the total amount of drug gives a good estimate of the amount of drug dissolved in the polymer at room temperature. The data are summarized in Table 1 and show that approximately 13% w/w of itraconazole is dissolved in eudragit E100. This phase separation starts from 13% drug loading and results in the appearance of glassy clusters of drug when extruded at 453K. These clusters experience no protective effect from the surrounding polymer and recrystallization results. It is well described that molecular dispersions and so called solid solutions have higher physical stability due to the antiplasticizing effect and protection against recrystallization from the surrounding polymer [1, 2].

Figure 5:
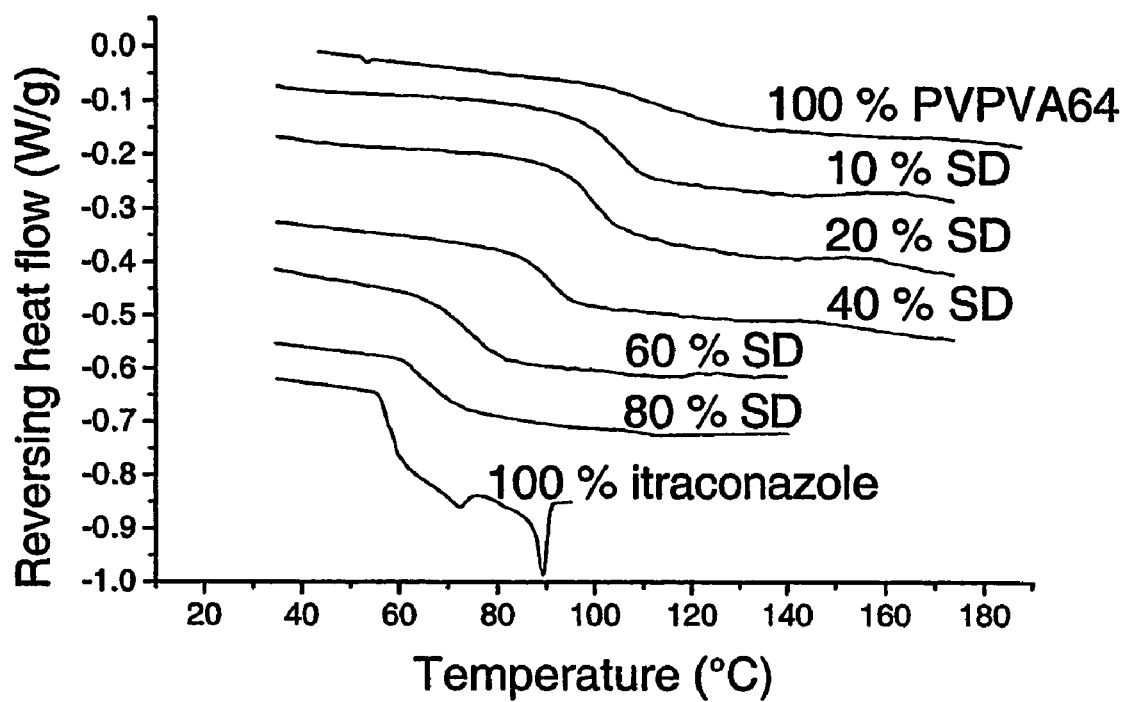

In a next set of experiments, extrudates were prepared with a fast dissolving polymer, PVPVA64. The extrusion parameters were identical to those of the extrudates with Eudragit E100 with the last two temperature zones fixed at 448.0, and 452.0K. The extrudates were milled and sieved and evaluated by MTDSC. FIG. 5 shows the reversing heat flow versus temperature of dispersions with different drug loading. It is clear that the drug is completely miscible with PVPVA64 (formation of molecular dispersion) because of the presence of one single Tg. The drug dissolves in all concentrations in the carrier with an increase in Tg because of the antiplasticizing effect of the polymer. These experimental Tg's can be compared to the theoretical ones calculated with the Gordon-Taylor equation to evaluate the miscibility and possible interaction. FIG. 6 shows that the theoretical and experimental values do not differ significantly proving the complete miscibility and volume additivity. It is well established that these dispersions will have a much higher stability than the dispersions with eudragit E100, because of the total miscibility and therefore the ideal situation for the protecting properties of the polymer.

An increase in dissolution rate and solubility has been reported for several amorphous drugs [11]. From FIG. 7 it is clear that glassy itraconazole has a higher dissolution rate in aqueous medium compared to its crystalline modification. This improvement is well known because of the absence of a crystalline lattice and the high energy state of the glassy form, however only 14% of the glassy drug is dissolved after three hours, which is not satisfactory.

FIG. 8 shows the dissolution profiles of dispersions with eudragit E100 and PVPVA64 containing 40% w/w of drug prepared at 453.0K as well as the dissolution profile of a 40% drug and 60% eudragit E100 physical mixture. This drug concentration is selected because itraconazole is given in a dose of 200 mg. The dissolution of the class II drug in Eudragit E100 reaches a satisfactory level of 80% after 20 minutes, which is an enormous enhancement compared to the physical mixture and the glassy drug. Nevertheless after two hours precipitation of the drug from the (supersaturated) solution is observed. The dissolution profile of the class II drug in PVPVA64 shows no precipitation, but the dissolution rate and level is not satisfactory since only 45% of drug is dissolved after 4 hours. The results in FIGS. 7 and 8 indicate that not only the physicochemical state of the drug is important in improving the dissolution properties (comparison with physical mixture), but also the polymer. The high dissolution rate of the class II drug from the eudragit E100 dispersion results in part from the microenvironment. Pure eudragit E100 has a slower dissolution rate than PVPVA64 because of its pH-dependent solubility. Pure PVPVA64 is 100% dissolved already after 4 minutes (FIG. 9) while pure eudragit E100 dissolves much slower because at the polymer surface the pH is increased when some eudragit E100 goes into solution thereby retarding the remaining undissolved polymer. This slower dissolution of eudragit E100 itself enables the drug to dissolve faster from the dispersion compared to the pure glassy drug. The solubility of the class II drug is also much higher in eudragit E100 solution (open bars) than in PVPVA64 solution (closed bars)(FIG. 10). We can expand the above mentioned results to other polymers, having the same properties as Eudragit E100 with respect to dissolution behaviour. For example itraconazole shows a good dissolution profile when dispersed in HPMC because the polymer itself dissolves rather slowly as it first needs to swell. The results of our experiments show that the physical stability for the PVPVA64 extrudates will be greater than for the eudragit E100 samples since a true molecular dispersion is formed with PVPVA64. However the pharmaceutical performance of the PVPVA preparations was not satisfactory.

In a next set of experiments, extrudates of itraconazole (40% w/w) were prepared by combining eudragit E100 and PVPVA64. FIG. 11 shows that preparing extrudates with both polymers in different ratios leads to a two-phase system, one consisting of a itraconazole-eudragit E100 phase and another of a itraconazole-PVPVA64 phase. It is clear that in these dispersions no clusters of pure glassy drug are present, which are able to recrystallize and hence affecting the physical stability and pharmaceutical performance. All itraconazole is molecularly dispersed in either the eudragit E100 or the PVPVA64 phase. Extrudates with different polymer ratios were prepared to investigate the influence on miscibility and dissolution. The class II drug is dissolved in all polymer ratios in one of both phases. The dissolution profiles are given in FIGS. 12 and 13. FIG. 12 shows an improvement of dissolution rate already when 20/80 and 60/40 eudragit E100/PVPVA64 ratio are used. These improvements are significant compared to 100% PVPVA64 but still not satisfactory for practical use. The 70/30 and 80/20 ratios (FIG. 13) however have a significant improvement in dissolution rate, which is even better than 100% eudragit E100. Precipitation does not occur because PVPVA64 has a stabilizing effect on itraconazole in solution, which is clearly seen in the dissolution profile of 100% PVPVA64 and well described in literature [12].

The use of combined polymers in solid dispersions for drugs with low aqueous solubility (class II compounds) looks very promising and is a totally new invention. The combination of the improved stability properties of one polymer and improved dissolution properties of another makes this invention a powerful tool to tackle the dissolution and stability problems of solid dispersions in one preparation method. Not only eudragit E100 and PVPVA64 can be used but also other polymers with the same intrinsic characteristics are potentially useful to increase the dissolution profile and stability of class II drugs. Hot-stage extrusion was used in this report, but spray drying a solution of a class II drug and a polymer combination in a volatile organic solvent can also be assumed to be as effective.

REFERENCES

[1] T. Matsumoto, and G. Zografi, Pharm. Res., 16 (1999) 1722-1728.
[2] G. Van den Mooter, M. Wuyts, N. Blaton, R. Busson, P. Grobet, P. Augustijns, and R. Kinget, Eur. J. Pharm. Sci. 12 (2001) 261-269.
[3] G. L. Amidon, H. Lennernäs, V. P. Shah, and J. R. Crison, Pharm. Res., 12 (1995) 413-420
[4] K. Six, G. Verreck, J. Peeters, P. Augustijns, R. Kinget, and G. Van den Mooter, Int. J. Pharm., 213 (2001) 163-173.
[5] S. Gordon, and J. S. Taylor, J. Appl. Chem. 2 (1952) 493-500.
[6] F. N. Kelley, and F. Bueche, J. Pol. Sci. 50 (1961) 549-556.
[7] R. Simha, R. P. Boyer, J. Chem. Phys. 37 (1962) 1003.
[8] F. Damian, N. Blaton, H. Desseyn, K. Clou, P. Augustijns, L. Naesens, J. Balzarini, R. Kinget, G. Van den Mooter. J. Pharmacy and Pharmacology. (2001), 53: 1109-1116.
[9] G. Van den Mooter, J. Van den Brande, P. Augustijns, R. Kinget J. Thermal analysis and Calorimetry. (1999), 57, 493-507.
[10] K. Six, G. Verreck, J. Peeters, K. Binnemans, H. Berghmans; P. Augustijns, R. Kinget, and G. Van den Mooter, Thermochim. acta, 376 (2001), 175-181
[11] B. C. Hancock, and M. Parks, Pharm. Res., 17 (2000) 397-404.

[12] M. Tros de Ilarduya, C. Martin, M. Goni, M. Martinez-Oharriz. Drug dev. Ind. Pharm. (1998) 24: 295-300.

TABLE 1

Calculated values of the amount of crystalline and dissolved itraconazole in the solid dispersions prepared at 413K and milled.

| Percentage itraconazole in the dispersions (% w/w) | Enthalpy of fusion (J/g)(n = 3) | Estimated initial crystallinity of itraconazole (% w/w) | Estimated amount itraconazole dissolved (% w/w) |
| --- | --- | --- | --- |
| 5.0 | 0.0 | 0.0 | 5.0 |
| 10.0 | 0.0 | 0.0 | 10.0 |
| 20.0 | 5.5 | 6.5 | 13.5 |
| 25.0 | 9.7 | 11.4 | 13.6 |
| 40.0 | 23.0 | 27.0 | 13.0 |
| 60.0 | 39.7 | 46.8 | 13.2 |

The invention claimed is:

1. A solid dispersion comprising a poorly soluble bioactive compound, which has a solubility of less than 1 gram per liter in an aqueous environment, dispersed in a polymer matrix that comprises a first polymer comprising a copolymer of vinylpyrrolidone and vinylacetate, and a second polymer that has a dissolution profile associated with the creation of a micro-environment enhancing the dissolution of the bioactive compound in said aqueous environment, wherein said second polymer comprises a cationic polymer based on dimethylaminoethyl methacrylate and neutral methacrylic ester, and wherein said first polymer and said second polymer are present in a ratio of 70-80 percent by weight of said first polymer to 20-30 percent by weight of said second polymer.

2. The solid dispersion according to claim 1 wherein at least one of said first and said second polymers has a stabilizing effect on the bioactive compound in solution.

3. The solid dispersion according to claim 1 wherein the bioactive compound is a class II drug in the Biopharmaceutical Classification System.

4. The solid dispersion according to claim 1 wherein the bioactive compound is a class IV drug in the Biopharmaceutical Classification System.

5. The solid dispersion according to claim 1 wherein the aqueous environment is a gastro-intestinal fluid.

6. The solid dispersion according to claim 5 wherein the aqueous environment is a gastric fluid.

7. The solid dispersion according to claim 1 prepared by extrusion.

8. The solid dispersion according to claim 1 prepared by spray-drying.

9. A solid dispersion according to claim 1 wherein the first polymer allows a homogenous or molecular dispersion of the bioactive compound in the polymer matrix, and wherein said first polymer and said second polymer are present in a ratio of 70:30 percent by weight.

10. The solid dispersion according to claim 9 wherein at least one of said first and said second polymers has a stabilizing effect on the bioactive compound in solution.

11. The solid dispersion according to claim 9 wherein the bioactive compound is a class II drug in the Biopharmaceutical Classification System.

12. The solid dispersion according to claim 9 wherein the bioactive compound is a class IV drug in the Biopharmaceutical Classification System.

13. The solid dispersion according to claim 9 wherein the aqueous environment is a gastro-intestinal fluid.

14. The solid dispersion according to claim 9 wherein the aqueous environment is a gastric fluid.

15. The solid dispersion according to claim 9 prepared by extrusion.

16. The solid dispersion according to claim 9 prepared by spray-drying.

* * * * *